(12) United States Patent
Choi et al.

(10) Patent No.: US 12,742,748 B2
(45) Date of Patent: Sep. 22, 2026

(54) NEUROTRANSMITTER CONCENTRATION MEASURING APPARATUS FOR PROVIDING SECOND DERIVATIVE-BASED NEUROTRANSMITTER CONCENTRATION MEASUREMENT RESULT OF FAST-SCAN CYCLIC VOLTAMMETRY DATA AND METHOD THEREOF

(71) Applicant: Daegu Gyeongbuk Institute of Science and Technology, Daegu (KR)

(72) Inventors: Ji Woong Choi, Seoul (KR); Seong Tak Kang, Yeosu-si (KR); Yong Seok Oh, Daegu (KR); Jeong Rak Park, Anyang-si (KR); Yun Ho Jeong, Seoul (KR)

(73) Assignee: Daegu Gyeongbuk Institute of Science and Technology, Daegu (KR)

( * ) Notice: Subject to any disclaimer, the term of this patent is extended or adjusted under 35 U.S.C. 154(b) by 381 days.

(21) Appl. No.: 18/120,771

(22) Filed: Mar. 13, 2023

(65) Prior Publication Data

US 2023/0375502 A1 Nov. 23, 2023

(30) Foreign Application Priority Data

May 17, 2022 (KR) ........................ 10-2022-0059880

(51) Int. Cl.
*G01N 27/416* (2006.01)
*A61B 5/145* (2006.01)
(Continued)

(52) U.S. Cl.
CPC ......... *G01N 27/4163* (2013.01); *G01N 27/48* (2013.01); *G01N 33/9413* (2013.01); *A61B 5/14546* (2013.01)

(58) Field of Classification Search
CPC .. G01N 27/4163; G01N 27/48; G01N 27/327; G01N 27/3277; G01N 33/9406–944; A61B 5/14546
See application file for complete search history.

(56) References Cited

U.S. PATENT DOCUMENTS

2003/0015422 A1* 1/2003 Fritsch .............. G01N 27/3278 204/403.01
2012/0247978 A1* 10/2012 Zevenbergen ..... G01N 33/0047 204/414
2021/0341412 A1* 11/2021 Jang .................. G01N 27/3277

FOREIGN PATENT DOCUMENTS

KR 10-1069310 B1 10/2011
KR 10-2020-0088358 A 7/2020
KR 10-2192043 B1 12/2020

OTHER PUBLICATIONS

John et al., "Chapter 4 Fast Scan Cyclic Voltammetry of Dopamine and Serotonin in Mouse Brain Slices," Michael AC, Borland LM, editors. Electrochemical Methods for Neuroscience. Boca Raton (FL): CRC Press/Taylor & Francis; 2007 (Year: 2007).*

(Continued)

*Primary Examiner* — Alexander S Noguerola
(74) *Attorney, Agent, or Firm* — Sughrue Mion, PLLC

(57) ABSTRACT

Disclosed is a technology of extracting faradaic current-type Second-Derivative-based Background Removal (SDBR) data, from which a capacitive charge current is subtracted, through the second derivative after background subtraction of FSCV data and providing a neurotransmitter concentration measurement result based on the extracted SDBR data. More particularly, a neurotransmitter concentration measuring apparatus according to an embodiment of the present disclosure includes a data collector configured to collect Fast-Scan Cyclic Voltammetry (FSCV) data in which a capacitive charge current is reflected in a faradaic current (Continued)

that changes according to neurotransmitter injection; a data processor configured to process the FSCV data as the faradaic current-type Second-Derivative-based Background Removal (SDBR) data, from which the capacitive charge current is subtracted, based on the second derivative for a voltage of an individual voltammogram generated for each scan by background subtraction in the FSCV data; and a measurement result provider configured to provide a concentration measurement result of a neurotransmitter that changes according to the neurotransmitter injection based on the SDBR data.

11 Claims, 11 Drawing Sheets

(51) Int. Cl.
*G01N 27/48* (2006.01)
*G01N 33/94* (2006.01)

(56) References Cited

OTHER PUBLICATIONS

Puthongkham et al., "Recent Advances in Fast-Scan Cyclic Voltammetry," Analyst. Feb. 17, 2020; 145(4): 1087-1102 (Year: 2020).*
Justin A. Johnson, et al., "Failure of Standard Training Sets in the Analysis of Fast-Scan Cyclic Voltammetry Data", ACS Chem Neurosci., Mar. 16, 2016, vol. 7, No. 3, 349-359 (22 pages).

* cited by examiner

FIG. 4
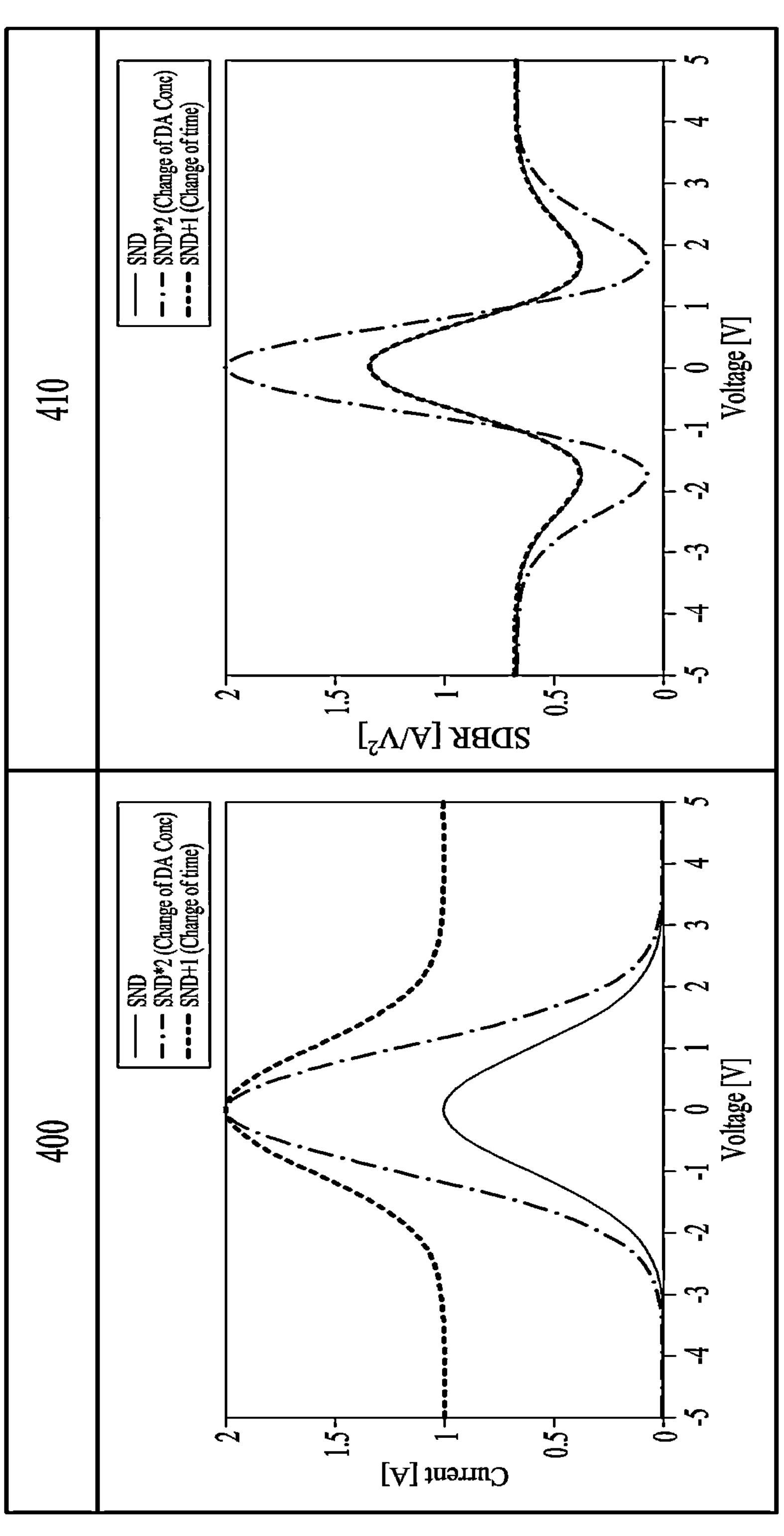
400
410
SND
SND*2 (Change of DA Conc)
SND+1 (Change of time)
Current [A]
SDBR [A/V²]
Voltage [V]
2
1.5
1
0.5
0
-5
-4
-3
-2
-1
0
1
2
3
4
5

FIG. 7A
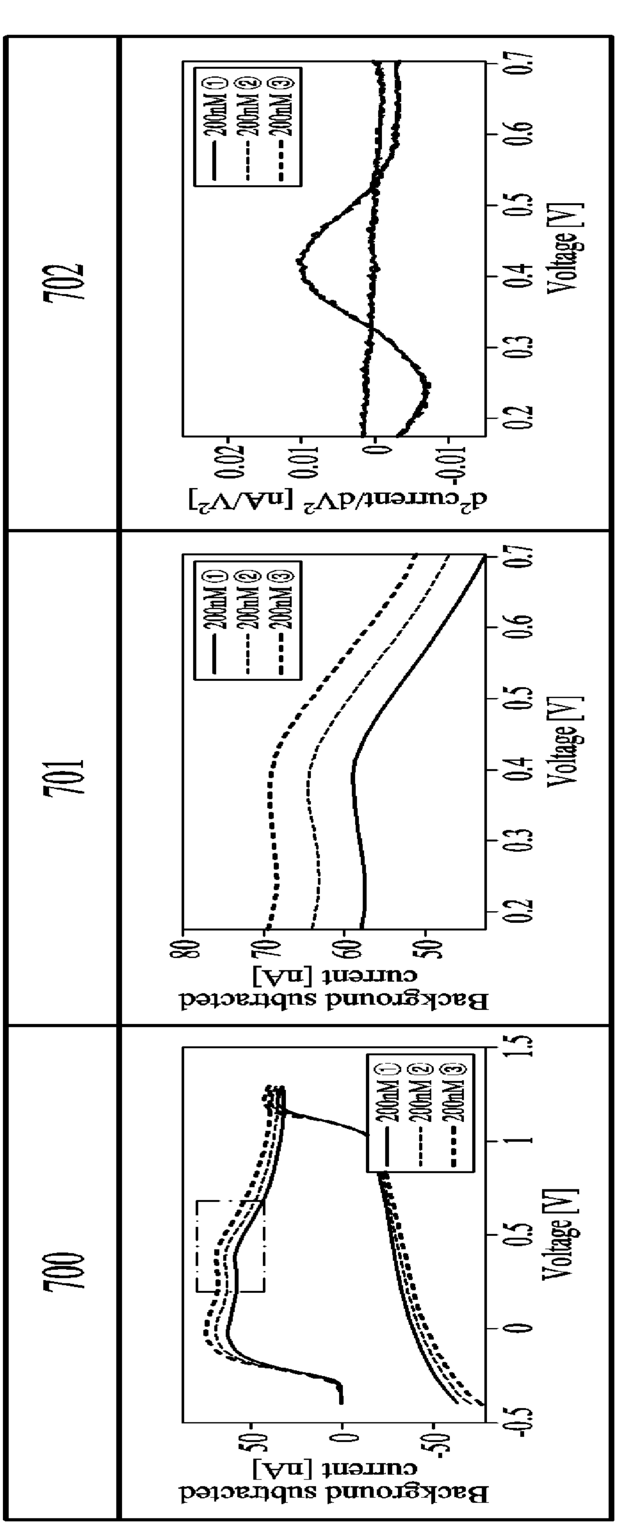

NEUROTRANSMITTER CONCENTRATION MEASURING APPARATUS FOR PROVIDING SECOND DERIVATIVE-BASED NEUROTRANSMITTER CONCENTRATION MEASUREMENT RESULT OF FAST-SCAN CYCLIC VOLTAMMETRY DATA AND METHOD THEREOF

CROSS-REFERENCE TO RELATED APPLICATION

This application claims priority to Korean Patent Application No. 10-2022-0059880, filed on May 17, 2022 in the Korean Intellectual Property Office, the disclosure of which is incorporated herein by reference.

BACKGROUND OF THE DISCLOSURE

Field of the Disclosure

The present disclosure relates to a neurotransmitter concentration measuring apparatus for providing a second derivative-based neurotransmitter concentration measurement result of Fast-Scan Cyclic Voltammetry (FSCV) data, and a method thereof, and more particularly to a technology of extracting faradaic current-type Second-Derivative-based Background Removal (SDBR) data, from which a capacitive charge current is subtracted, through second derivative after background subtraction of FSCV data and providing a neurotransmitter concentration measurement result based on the extracted SDBR data.

Description of the Related Art

Dopamine, which acts as a neurotransmitter in the brain, is a neuromodulator that transmits important information such as cognition, reward and pleasure, and voluntary movement, and dysregulation of the dopamine system is associated with a wide range of brain disorders such as Parkinson's disease, Tourette's syndrome, addiction and schizophrenia.

Dopamine levels in target regions of the brain show highly dynamic changes and fluctuate according to different time scales.

Such a change may include a sudden transient phenomenon (phasic), which are ramps that can last for several seconds, and slow oscillations (tonic) ranging from minutes to hours.

Quantitative analysis of dopamine levels is important for learning about the functional role of dopamine dynamics in the normal brain and studying the pathology of brain disorders in preclinical and clinical studies.

Figure 1:
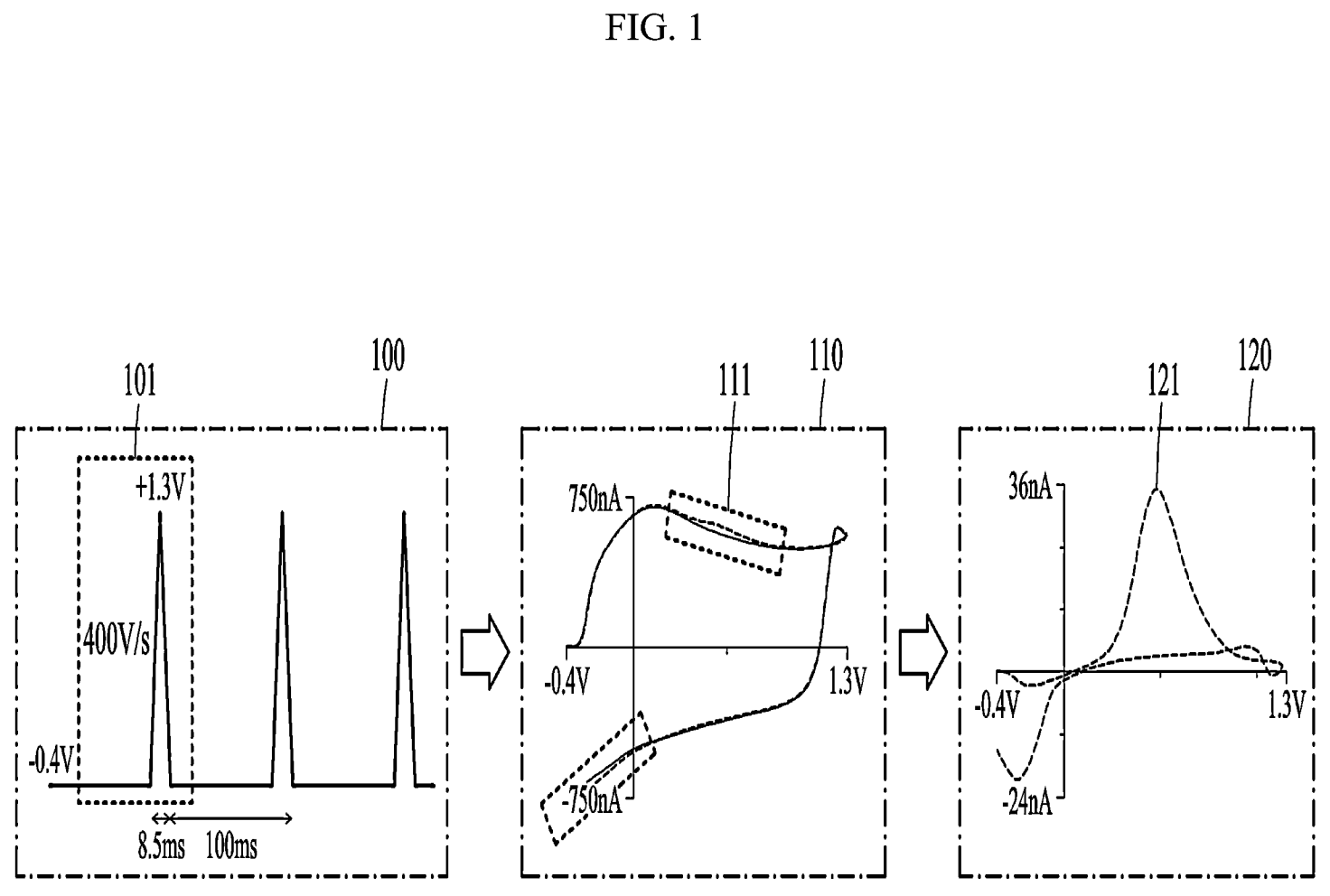

FIG. 1 is a diagram explaining the measurement of a neurotransmitter based on Fast-Scan Cyclic Voltammetry (FSCV) according to a related technology.

Referring to FIG. 1, a graph 100 illustrates a standard FSCV voltage waveform applied at 10 Hz for dopamine measurement, a graph 110 illustrates a background voltammogram measured during voltage change, and a voltammogram when dopamine is present, and a graph 120 illustrates a voltammogram of the graph 110 from which the background is removed.

FSCV using a Carbon Fiber Minute Electrode (CFM) is a well-established electrochemical technique that can effectively measure changes in dopamine levels in the brain.

FSCV measures a faradaic current change based on a dopamine oxidation peak voltage shown in a voltammogram after subtracting a background current.

The current according to the voltage measured in a current change region 101 shown in the graph 100 is converted into the graph 110, and a region 111 in the graph 110 represents a voltammogram when dopamine is present. The result of background subtraction, which subtracts the background except for the region 111, may be as shown in the graph 120, and a peak 121 may be identified in the graph 120.

However, the FSCV's high scan rate is sensitive enough to measure sudden changes in dopamine levels (phasic dopamine), but it may also create a progressively larger background charge current (capacitive charge currents), making it difficult to analyze voltage/current exceeding 2 minutes.

A steady rise in the dopamine peak amplitude of FSCV due to the background charge current is called background drift.

The FSCV background drift makes it difficult to measure slow changes in dopamine levels (tonic dopamine).

There are still difficulties in measuring tonic dopamine levels in the brain in real-time, so a modified voltammetry method was proposed to measure tonic dopamine in vivo.

The modified voltage/current measurement technique can measure tonic dopamine levels, but has difficulties in analyzing detailed dopamine signals for understanding neuropsychiatric disorders due to their low time resolution (10 to 20 seconds).

The high-pass filtering technology can measure a phase dopamine from which background drift has been subtracted, but has a problem in that it can also remove tonic dopamine levels with a frequency band similar to background drift.

FSCV is a technology that measures a concentration change of an analyte in real-time by measuring a current that changes according to the degree of oxidation and reduction of the analyte near an electrode during rapid voltage change. In particular, FSCV has been widely used to measure the rapidly changing dopamine concentration.

The high scan rate of the FSCV makes it possible to sensitively measure a neurotransmitter (e.g., dopamine), but, at the same time, may generate a progressively larger capacitive current.

Accordingly, only changes in a neurotransmitter concentration which occur within 1 to 2 minutes faster than the rate at which a capacitive current occurs can be analyzed.

Therefore, the FSCV was chronically unable to observe slow changes in dopamine concentration during measurements of 2 minutes or more.

This is slowing progress in all brain science research based on understanding the neurotransmitter systems in the brain.

RELATED ART DOCUMENTS

Patent Documents (Patent Document 1) Korean Patent No. 10-2192043, "A METHOD FOR MEASURING PHASE TRANSITION OF TEMPERATURE-SENSITIVE POLYMERS AND A DEVICE FOR MEASURING CONCENTRATION"

(Patent Document 2) US Patent No. 2021/0341412, "MEASURING NEUROCHEMICAL LEVELS WITH MULTIPLE CYCLIC SQUARE WAVE VOLTAMMETRY"

(Patent Document 3) Korean Patent No. 10-1069310, "ELECTROCHEMICAL BIOSENSOR WITH CONDUCTING POLYMER-MODIFIED ELECTRODES FOR A SIMULTANEOUS DETECTION OF DOP-

AMINE, ASCORBIC ACID AND URIC ACID AND METHOD OF PREPARING THE SAME"

(Patent Document 4) Korean Patent Application Publication No. 10-2020-0088358, "CALIBRATION FREE IN-VIVO MEASUREMENT OF ANALYTES USING ELECTROCHEMICAL SENSORS"

SUMMARY OF THE DISCLOSURE

Therefore, the present disclosure has been made in view of the above problems, and it is an object of the present disclosure to provide a technology of extracting faradaic current-type Second-Derivative-based Background Removal (SDBR) data, from which a capacitive charge current is subtracted, through second derivative after background subtraction of Fast Scan Cyclic Voltammetry (FSCV) data and providing a neurotransmitter concentration measurement result based on the extracted SDBR data.

It is another object of the present invention to additionally provide slow dopamine concentration change information to all standard FSCV data measured such that only fast dopamine concentration changes can be limitedly seen, by providing an additional slow dopamine change degree to fast dopamine information that can be measured with high sensitivity with the standard FSCV because the present disclosure extracts slow dopamine change information through post-processing while using the standard FSCV as it is.

It is still another object of the present invention to improve the accessibility of neuroscientists who want to measure the concentration of a neurotransmitter using the standard FSCV data because the input voltage waveform of the standard FSCV can be used as it is.

It is yet another object of the present invention to improve the detailed analysis rate of a signal of dopamine, which is a neurotransmitter, because it can extract a faradaic current form of a neurotransmitter regardless of a capacitive charge current, thereby improving the temporal resolution.

In accordance with an aspect of the present invention, the above and other objects can be accomplished by the provision of a neurotransmitter concentration measuring apparatus, including: a data collector configured to collect FSCV data in which a capacitive charge current is reflected in a faradaic current that changes according to neurotransmitter injection; a data processor configured to process the FSCV data as the faradaic current-type SDBR data, from which the capacitive charge current is subtracted, based on second derivative for a voltage of an individual voltammogram generated for each scan by background subtraction in the FSCV data; and a measurement result provider configured to provide a concentration measurement result of a neurotransmitter that changes according to the neurotransmitter injection based on the SDBR data.

The data processor may extract the individual voltammogram in which the faradaic current and the capacitive charge current are reflected together for each scan by the background subtraction in relation to a peak according to neurotransmitter injection in the FSCV data, and may process as the SDBR data by quantifying a curvature of a neurotransmitter peak by multiplying the extracted individual voltammogram by a negative value after the second derivative for the voltage of the extracted individual voltammogram.

The extracted individual voltammogram may include a phasic measurement result in relation to measuring a concentration of the neurotransmitter, and the SDBR data includes the phasic measurement result and tonic measurement result in relation to measuring a concentration of the neurotransmitter.

The data processor may extract the individual voltammogram such that, after the background subtraction, a voltammogram around a neurotransmitter oxidation peak has a symmetrical Gaussian shape.

The data processor may process the SDBR data such that an amplitude current of a neurotransmitter oxidation peak of a voltammogram corresponding to the individual voltammogram is linearly correlated with a concentration of the neurotransmitter and such that a background charging current generated around the neurotransmitter oxidation peak is independent of voltage.

The measurement result provider may determine a neurotransmitter oxidation peak voltage based on the faradaic current type from which the capacitive charge current based on the SDBR data is subtracted, and may provide a neurotransmitter concentration, compared to the determined neurotransmitter oxidation peak voltage, as a neurotransmitter concentration measurement result.

The data collector may collect the FSCV data in which a faradaic current increasing at a time of the neurotransmitter injection and the capacitive charge current gradually increasing over time are combined.

In accordance with another aspect of the present invention, there is provided a neurotransmitter concentration measurement method, including: collecting, by a data collector, FSCV data in which a capacitive charge current is reflected in a faradaic current that changes according to neurotransmitter injection; processing, by a data processor, the FSCV data as the faradaic current-type SDBR data, from which the capacitive charge current is subtracted, based on second derivative for a voltage of an individual voltammogram generated for each scan by background subtraction in the FSCV data; and providing, by a measurement result provider, a concentration measurement result of a neurotransmitter that changes according to the neurotransmitter injection based on the SDBR data.

The processing may include extracting the individual voltammogram in which the faradaic current and the capacitive charge current are reflected together for each scan by the background subtraction in relation to a peak according to neurotransmitter injection in the FSCV data, and processing as the SDBR data by quantifying a curvature of a neurotransmitter peak by multiplying the extracted individual voltammogram by a negative value after the second derivative for the voltage of the extracted individual voltammogram.

The extracted individual voltammogram may include a phasic measurement result in relation to measuring a concentration of the neurotransmitter, and the SDBR data may include the phasic measurement result and tonic measurement result in relation to measuring a concentration of the neurotransmitter.

The processing may include: extracting the individual voltammogram such that, after the background subtraction, a voltammogram around a neurotransmitter oxidation peak has a symmetrical Gaussian shape; and processing the SDBR data such that an amplitude current of a neurotransmitter oxidation peak of a voltammogram corresponding to the individual voltammogram is linearly correlated with a concentration of the neurotransmitter and such that a background charging current generated around the neurotransmitter oxidation peak is independent of voltage.

The providing may include determining a neurotransmitter oxidation peak voltage based on the faradaic current type from which the capacitive charge current based on the SDBR data is subtracted; and providing a neurotransmitter concentration, compared to the determined neurotransmitter oxidation peak voltage, as a neurotransmitter concentration measurement result.

The collecting may include collecting the FSCV data in which a faradaic current increasing at a time of the neurotransmitter injection and the capacitive charge current gradually increasing over time are combined.

BRIEF DESCRIPTION OF THE DRAWINGS

The above and other objects, features and other advantages of the present disclosure will be more clearly understood from the following detailed description taken in conjunction with the accompanying drawings, in which:

FIG. 1 is a diagram explaining the measurement of a neurotransmitter based on Fast-Scan Cyclic Voltammetry (FSCV) according to a related technology;

FIG. 2 illustrates a neurotransmitter concentration measuring apparatus according to an embodiment of the present disclosure;

FIG. 4 illustrates drawings for comparing standard normal distribution-shaped voltammetry models of a second-derivative-based background drift removal (SDBR) result according to an embodiment of the present invention and an existing background subtraction result;

FIGS. 5 to 7B illustrate a neurotransmitter concentration measurement process based on standard FSCV data by a neurotransmitter concentration measuring apparatus according to an embodiment of the present disclosure;

DETAILED DESCRIPTION OF THE DISCLOSURE

Figure 3:
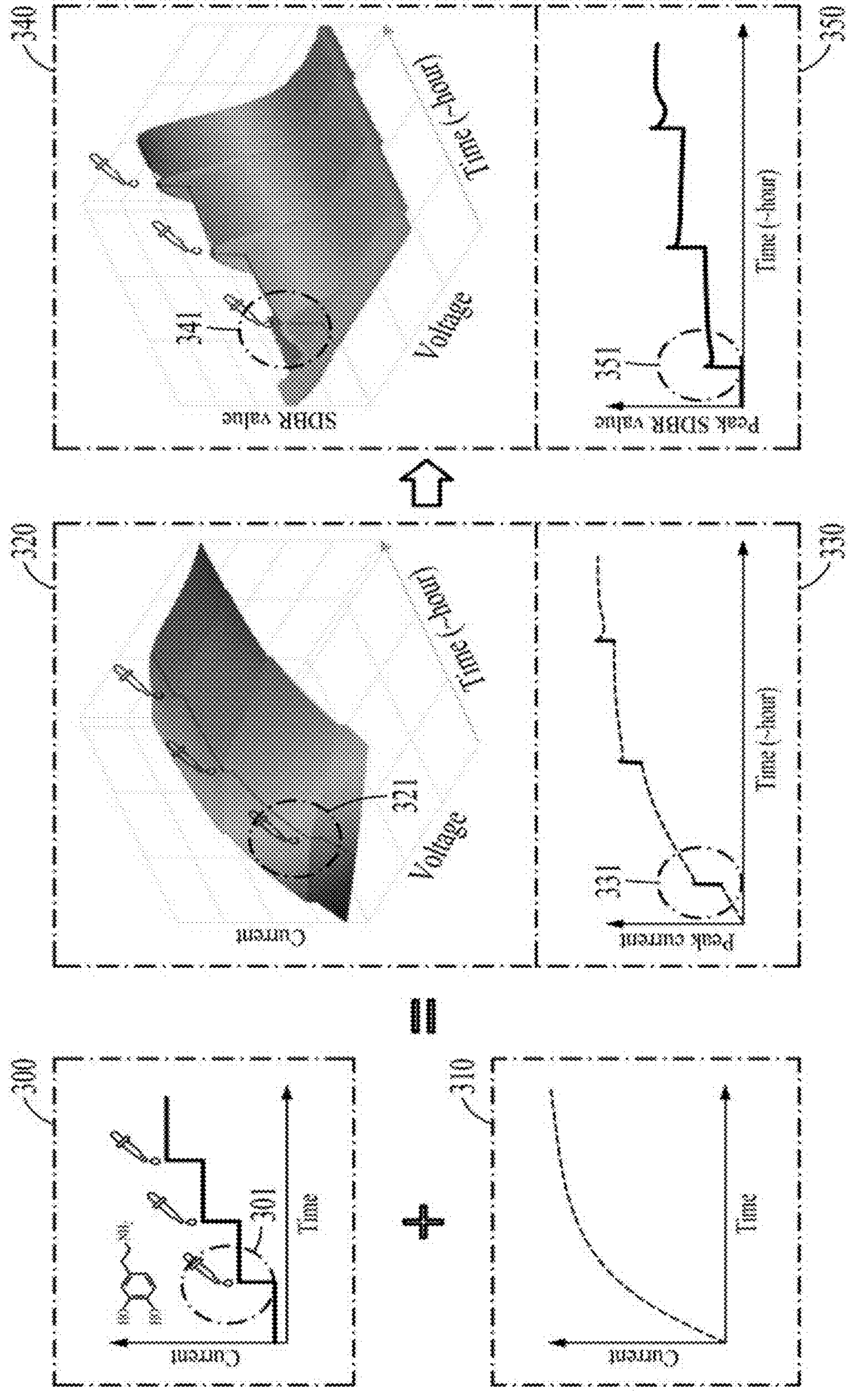
FIG. 3 illustrates a process of extracting a faradaic current in relation to a neurotransmitter concentration by a neurotransmitter concentration measuring apparatus according to an embodiment of the present disclosure.

Specific structural and functional descriptions of embodiments according to the concept of the present disclosure disclosed herein are merely illustrative for the purpose of explaining the embodiments according to the concept of the present disclosure. Furthermore, the embodiments according to the concept of the present disclosure can be implemented in various forms and the present disclosure is not limited to the embodiments described herein.

The embodiments according to the concept of the present disclosure may be implemented in various forms as various modifications may be made. The embodiments will be described in detail herein with reference to the drawings. However, it should be understood that the present disclosure is not limited to the embodiments according to the concept of the present disclosure, but includes changes, equivalents, or alternatives falling within the spirit and scope of the present disclosure.

The terms such as "first" and "second" are used herein merely to describe a variety of constituent elements, but the constituent elements are not limited by the terms. The terms are used only for the purpose of distinguishing one constituent element from another constituent element. For example, a first element may be termed a second element and a second element may be termed a first element without departing from the scope of rights according to the concept of the present invention.

It will be understood that when an element is referred to as being "on", "connected to" or "coupled to" another element, it may be directly on, connected or coupled to the other element or intervening elements may be present. In contrast, when an element is referred to as being "directly on," "directly connected to" or "directly coupled to" another element or layer, there are no intervening elements or layers present. Other words used to describe the relationship between elements should be interpreted in a like fashion (e.g., "between," versus "directly between," "adjacent," versus "directly adjacent," etc.).

The terms used in the present specification are used to explain a specific exemplary embodiment and not to limit the present inventive concept. Thus, the expression of singularity in the present specification includes the expression of plurality unless clearly specified otherwise in context. Also, terms such as "include" or "comprise" in the specification should be construed as denoting that a certain characteristic, number, stage, operation, constituent element, component or a combination thereof exists and not as excluding the existence of or a possibility of an addition of one or more other characteristics, numbers, stages, operations, constituent elements, components or combinations thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present disclosure will now be described more fully with reference to the accompanying drawings, in which exemplary embodiments of the invention are shown. This disclosure may, however, be embodied in many different forms and should not be construed as limited to the exemplary embodiments set forth herein. Like reference numerals in the drawings denote like elements.

Figure 2:
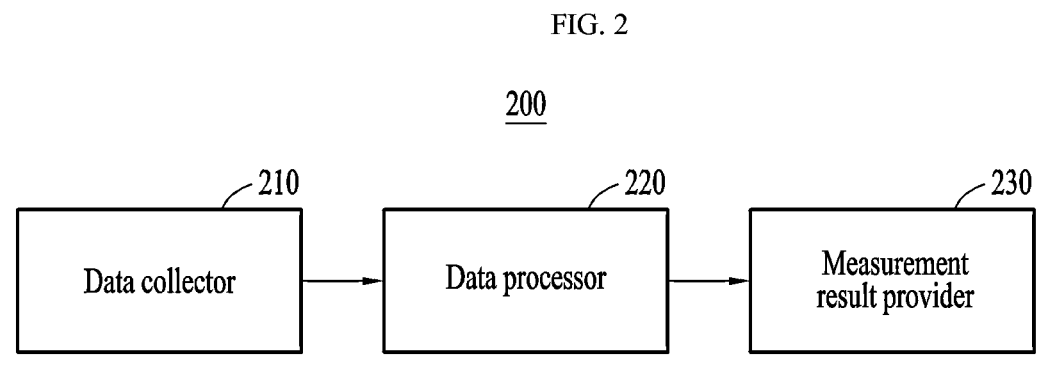

FIG. 2 illustrates a neurotransmitter concentration measuring apparatus according to an embodiment of the present disclosure.

FIG. 2 exemplifies components of a neurotransmitter concentration measuring apparatus according to an embodiment of the present disclosure.

Referring to FIG. 2, a neurotransmitter concentration measuring apparatus 200 according to an embodiment of the present disclosure includes a data collector 210, a data processor 220 and a measurement result provider 230.

For example, the data collector 210, the data processor 220 and the measurement result provider 230 may be components functionally operated by a processor.

According to an embodiment of the present disclosure, the data collector 210 may collect Fast-Scan Cyclic Voltammetry (FSCV) data in which a capacitive charge current is reflected in a faradaic current that changes according to neurotransmitter injection.

For example, the data collector 210 may collect FSCV data in which a faradaic current, which increases at the time of neurotransmitter injection, and a capacitive charge current, which gradually increases over time, are combined.

For example, the FSCV data is data for measuring changes in neurotransmitter levels in the brain in real-time, uses a voltage waveform applied to measure dopamine, which is a neurotransmitter, as basic data, and may refer to data that can be converted into a background voltammogram measured during voltage change and a voltammogram when a neurotransmitter is present.

In addition, the FSCV data may be configured in the form of a combination of stepwise faradaic current and capacitive charge current according to dopamine injection in time change.

According to an embodiment of the present disclosure, the data processor 220 may process the FSCV data to faradaic current-type Second-Derivative-based Background Removal (SDBR) data, from which a capacitive charge current has been subtracted, based on the second derivative of the voltage of an individual voltammogram generated for each scan by background subtraction from the FSCV.

That is, the data processor 220 may extract the individual voltammogram in which a faradaic current and a capacitive charge current are reflected together for each scan by background subtraction in relation to a peak according to neurotransmitter injection in the FSCV data.

In addition, the data processor 220 may quantify the curvature of the neurotransmitter peak by multiplying the extracted individual voltammogram by a negative value after the second derivative for voltage and process it as SDBR data.

For example, the individual voltammogram extracted based on background subtraction includes a phasic measurement result in relation to measuring a concentration of the neurotransmitter, and thus may indicate a phasic measurement result.

Meanwhile, the SDBR data processed by the data processor 220 according to an embodiment of the present disclosure may include the phasic measurement result and tonic measurement result in relation to measuring a concentration of the neurotransmitter.

For example, the phasic measurement result may be related to a change in the concentration of a neurotransmitter that changes in a fast time, and the tonic measurement result may be related to a change in the concentration of a neurotransmitter that changes in a slow time. Here, the fast time may be a short time, and the slow time may be a long time.

In addition, the phasic measurement result is less affected by a capacitive charge current, but the tonic measurement result is greatly affected by a capacitive charge current, so the tonic measurement result may be different depending on the presence or absence of the capacitive charge current. In addition, the influence of the capacitive charge current is proportional to time.

According to an embodiment of the present disclosure, the data processor 220 may extract the individual voltammogram such that, after the background subtraction, a voltammogram around a neurotransmitter oxidation peak has a symmetrical Gaussian shape.

For example, the data processor 220 may process the SDBR data such that an amplitude current of a neurotransmitter oxidation peak of a voltammogram corresponding to the individual voltammogram is linearly correlated with a concentration of the neurotransmitter.

In addition, the data processor 220 may process SDBR data such that a background charging current generated around the neurotransmitter oxidation peak is independent of voltage.

According to an embodiment of the present disclosure, the measurement result provider 230 may provide a neurotransmitter concentration measurement result that changes according to neurotransmitter injection based on the SDBR data.

For example, the measurement result provider 230 may determine a neurotransmitter oxidation peak voltage based on the faradaic current type from which the capacitive charge current based on the SDBR data is subtracted, and may provide a neurotransmitter concentration, compared to the determined neurotransmitter oxidation peak voltage, as a neurotransmitter concentration measurement result.

Therefore, the present disclosure may extract faradaic current-type SDBR data, from which a capacitive charge current is subtracted through second derivative, after background subtraction of the FSCV data, and may provide a neurotransmitter concentration measurement result based on the extracted SDBR data.

FIG. 3 illustrates a process of extracting a faradaic current in relation to a neurotransmitter concentration by a neurotransmitter concentration measuring apparatus according to an embodiment of the present disclosure.

FIG. 3 exemplifies a process of extracting faradaic current-type SDBR data from which a capacitive charge current is subtracted through a second derivative after background subtraction of FSCV data to extract a faradaic current form which a capacitive charge current making long-time measurement impossible when using an existing FSCV data is subtracted.

Referring to FIG. 3, a graph 300 shows a faradaic current following the injection of dopamine, which is a neurotransmitter, over time, and a graph 310 shows a capacitive charge current over time.

In addition, a graph 320 three-dimensionally shows an individual voltammogram as a result of background subtraction for each scan applied to FSCV data in which the currents based on the graph 300 and the graph 310 are combined, and a graph 330 two-dimensionally shows the voltammogram.

Meanwhile, a graph 340 three-dimensionally shows SDBR data expressed by quantifying the curvature of a neurotransmitter peak by multiplying the data of the graph 320 by a negative value after the second derivative, and a graph 350 two-dimensionally shows the SDBR data.

In the graph 300, a point 301 indicates the point at which dopamine, which is a neurotransmitter, is injected, which corresponds to a point 321 in the graph 320, a point 331 in the graph 330, a point 341 in the graph 340 and a point 351 in the graph 350.

However, when comparing the point 301 with the point 331 and the point 351, it can be confirmed that the point 301 and the point 351 are similar, and that there is a difference between the point 331 and the point 301 due to the influence of a capacitive charge current.

This is because the neurotransmitter concentration measuring apparatus according to an embodiment of the present disclosure provides data on the graph 350 including the point 351 as a result of processing the SDBR data with a faradaic current, from which a capacitive charge current is removed, as SDBR data is processed with a result of applying the SDBR technique of multiplying the data of the point 331 by a negative value after the second derivative.

The SDBR data processing method may model a background-subtracted voltammogram around a neurotransmitter oxidation peak generated for each scan, and extract a specific scan time and dopamine oxidation peak voltage from the modeled voltammogram through Equation 1.

$$Voltgram_{BS}(\mathrm{V},t)=e^{-\frac{(V-peak_v)^2}{2}}Conc_{DA}+Charg_c(t) \quad \text{[Equation 1]}$$

In Equation 1, $Voltgram_{BS}$ represents a voltammogram to which background subtraction is applied, V represents an ambient voltage, t represents a specific scan time, $peak_v$ represents a dopamine oxidation peak, and $Conc_{DA}$ represents a dopamine concentration, and $Charge_c$ represents a background charging current.

By setting V to $peak_v$, a current of a dopamine oxidation peak of a voltammogram may be observed, and Equation 1 may be the same as Equation 2 below:

$$\mathrm{Voltgram}_{BS}(\mathrm{peak}_v,t)=\mathrm{Conc}_{DA}+\mathrm{Charg}_c(t) \quad \text{[Equation 2]}$$

In Equation 2 which represents a voltammogram with the current of $peak_v$ subtracted from a normal background, $Charg_c$ may be constantly maintained.

When $Charg_c$ is subtracted, an intrinsic curvature of a dopamine oxidation peak may be quantified by applying a second derivative for second derivative to each background-subtracted voltammogram, and expressed as in Equation 3 below:

$$Voltgram_{SDBR}(\mathrm{V},t)= \frac{-d^2}{dV^2}Voltgram_{BS}(\mathrm{V},t)=\left(1-(\mathrm{V}-\mathrm{peak}_v)^2\right)e^{-\frac{(V-peak_v)^2}{2}}Conc_{DA} \quad \text{[Equation 3]}$$

In Equation 3, $Voltgram_{SDBR}$ is SDBR data and may represent a voltammogram to which SDBR is applied.

After setting V to $peak_v$ and second derivative of the modeled voltammogram, a dopamine peak current may be observed. Equation 3 may be the same as Equation 4 below:

$$\frac{-d^2}{dV^2}Voltgram_{BS}(\mathrm{peak}_v,t)=Conc_{DA} \quad \text{[Equation 4]}$$

According to Equation 4, it can be confirmed that a capacitive charge current is subtracted from an individual voltammogram obtained by background subtraction from FSCV data, and only a faradaic current remains.

According to an embodiment of the present disclosure, the neurotransmitter concentration measuring apparatus may extract the form of a neurotransmitter faradaic current regardless of a capacitive charge current by multiplying a negative value after the second derivative of the voltage in the voltammogram at each time and by quantifying the curvature of the peak so as to extract a faradaic current form which a capacitive charge current making it impossible to measure a long time of FSCV is subtracted.

FIG. 4 illustrates drawings for comparing standard normal distribution-shaped voltammetry models of a second-derivative-based background drift removal (SDBR) result according to an embodiment of the present invention and an existing background subtraction result.

Referring to FIG. 4, a graph 400 illustrates background subtraction results according to a dopamine concentration and a charging current in a standard normal distribution (SND)-shaped voltammogram model, and a graph 410 illustrates SDBR results according to a dopamine concentration and a charging current in an SND-shaped voltammogram.

In the Gaussian voltammogram of the background subtraction results of the graph 400, a standard normal distribution is represented by SND, an increase in a charging current over time is represented by addition SND+1, and an increase in a dopamine level is represented by multiplication SND*2.

Meanwhile, in the Gaussian voltammogram model of the SDBR results of the graph 410, a standard normal distribution is represented by SND, an increase in a charging current over time is represented by addition SND+1, and an increase in a dopamine level is represented by multiplication SND*2.

The graphs 400 and 410 show background subtraction results and SDBR results according to charging current and dopamine level.

The concentration change may be expressed as a linear product of the Gaussian model, and a charging current according to a change in time may be expressed as an addition.

In a general background subtraction model, peak current measurement cannot distinguish between an increase in a charging current due to a change in time and an increase in current due to a change in a dopamine concentration.

However, in a voltammogram model to which SDBR is applied, it can be confirmed that the same peak current is displayed at the same concentration regardless of the passage of time by subtracting the influence of a charging current.

In addition, it can be confirmed that the increased dopamine concentration is expressed as a linear increase in SDBR peak current.

FIGS. 5 to 7B illustrate a neurotransmitter concentration measurement process based on standard FSCV data by a neurotransmitter concentration measuring apparatus according to an embodiment of the present disclosure.

FIGS. 5 to 7B illustrate background subtraction results and SDBR in vitro test results which are obtained using standard FSCV data by the neurotransmitter concentration measuring apparatus according to an embodiment of the present disclosure.

In other words, FIGS. 5 to 7B are test results to measure phasic and tonic dopamine concentrations using standard FSCV.

Figure 5:
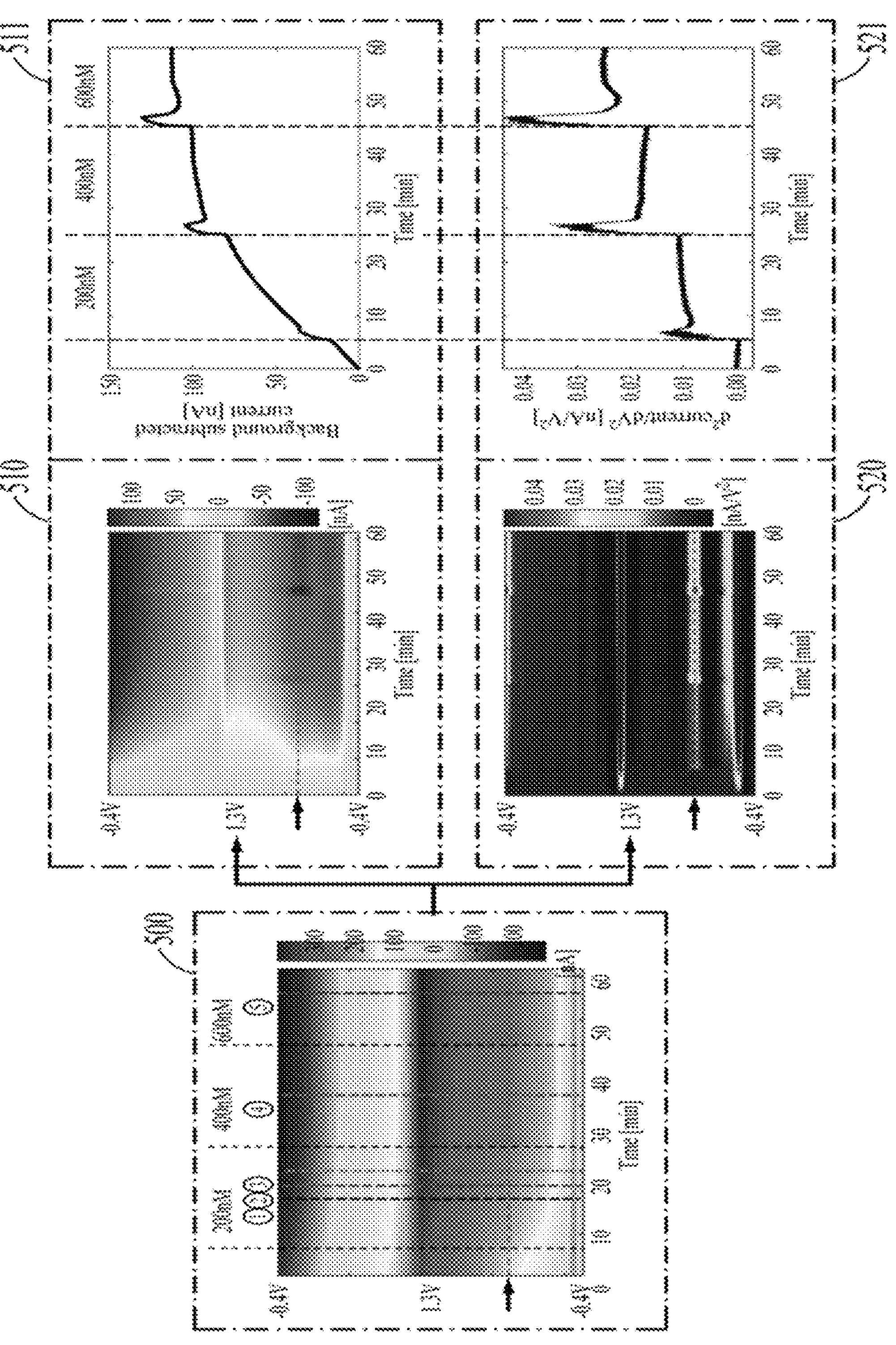

Referring to FIG. 5, a graph 500 represents raw data, graphs 510 and 511 represent background subtraction data, and graphs 520 and 521 represent SDBR data.

The graph 500 shows a raw FSCV color plot in an in vitro test. In the graph, black dotted lines indicate the timing of injection of 200 nm dopamine droplets.

In addition, the numbers indicated by each circle and the corresponding lines are related to voltammograms of specific times to be described with reference to FIGS. 7A and 7B.

The graphs 510 and 511 show the color plots and current changes of the dopamine peaks over time based on the background subtraction results.

The graphs 520 and 521 show the color plots and current changes of the dopamine peaks over time based on the SDBR results.

Dopamine (200 nM) was added dropwise to a PBS solution every 20 min and allowed to stir for 2 min.

The graph 500 shows that the standard FSCV measures a faradaic current due to dopamine around CFM and that a capacitive current change is gradually generated due to a high scan rate.

The graphs 510 and 511 show results of applying the background subtraction technique to observe phasic dopamine levels according to the existing technology.

However, as shown in the graphs 510 and 511, it was confirmed that even at the same dopamine concentration, a capacitive current causing a sustained current rise makes it difficult to analyze changes in tonic dopamine levels.

The continuous increase in the capacitive current over time can be seen in the graph 511.

In contrast, the graph 521, which presents results based on the SDBR data, shows flatness with similar values at the same concentration over a 1-hour experiment without background drift.

Figure 6:
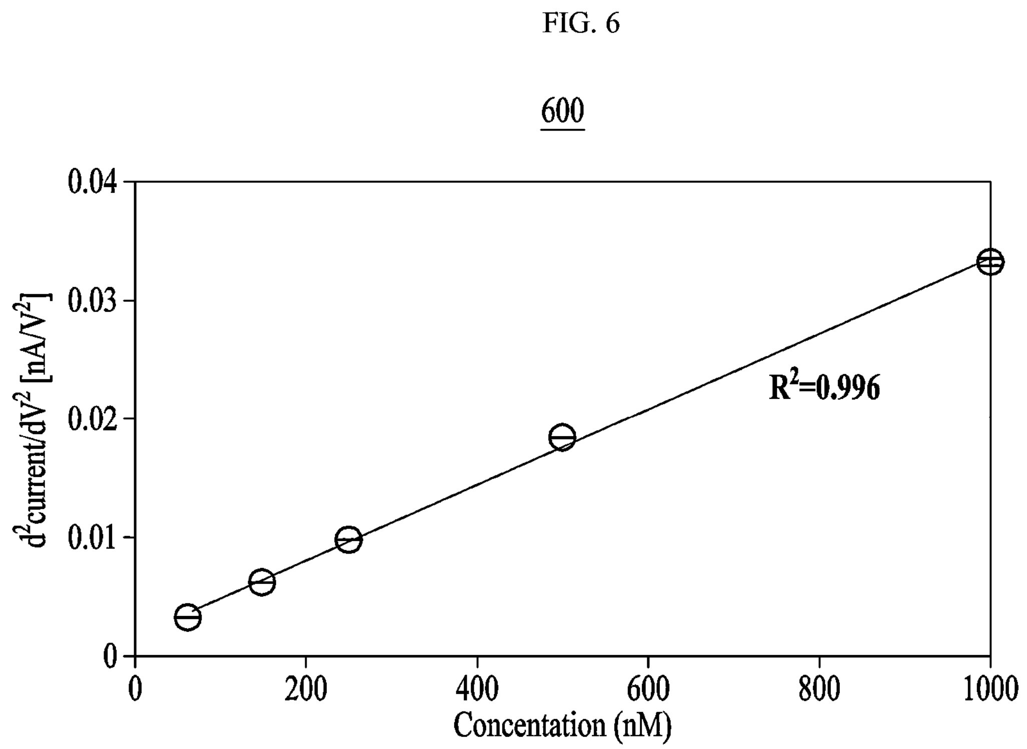

Referring to FIG. 6, a graph 600 shows a correlation between current and concentration multiplied by a negative value after second derivative according to an SDBR correction plot.

In other words, the graph 600 shows an SDBR calibration plot, and the SDBR signal may represent a correlation with a tonic dopamine concentration.

The ellipse in the graph 600 indicates the injection time of dopamine, which is a neurotransmitter. Here, the concentration increases with increasing current.

For example, the detection limit may be 8.16±0.08 nM which is sufficient for dopamine measurement in vivo.

FIG. 7A shows voltammogram changes in ①, ②, and ③ in the graph 500 of FIG. 5 at 2-minute intervals at the same dopamine concentration of 200 nM.

Referring to FIG. 7A, a result obtained by applying the background subtraction technique to the dotted square in a graph 700 corresponds to a graph 701, and an SDBR result for the graph 701 corresponds to a graph 702.

In the graphs 700 and 701, it can be confirmed that voltammograms at 2-minute intervals have a similar shape near a dopamine oxidation peak, but the amplitude steadily increases due to the capacitive current.

Meanwhile, the graph 702 shows that the SDBR values of the dopamine oxidation peaks are almost the same under the same concentration condition, regardless of the lapse of time.

Figure 7B:
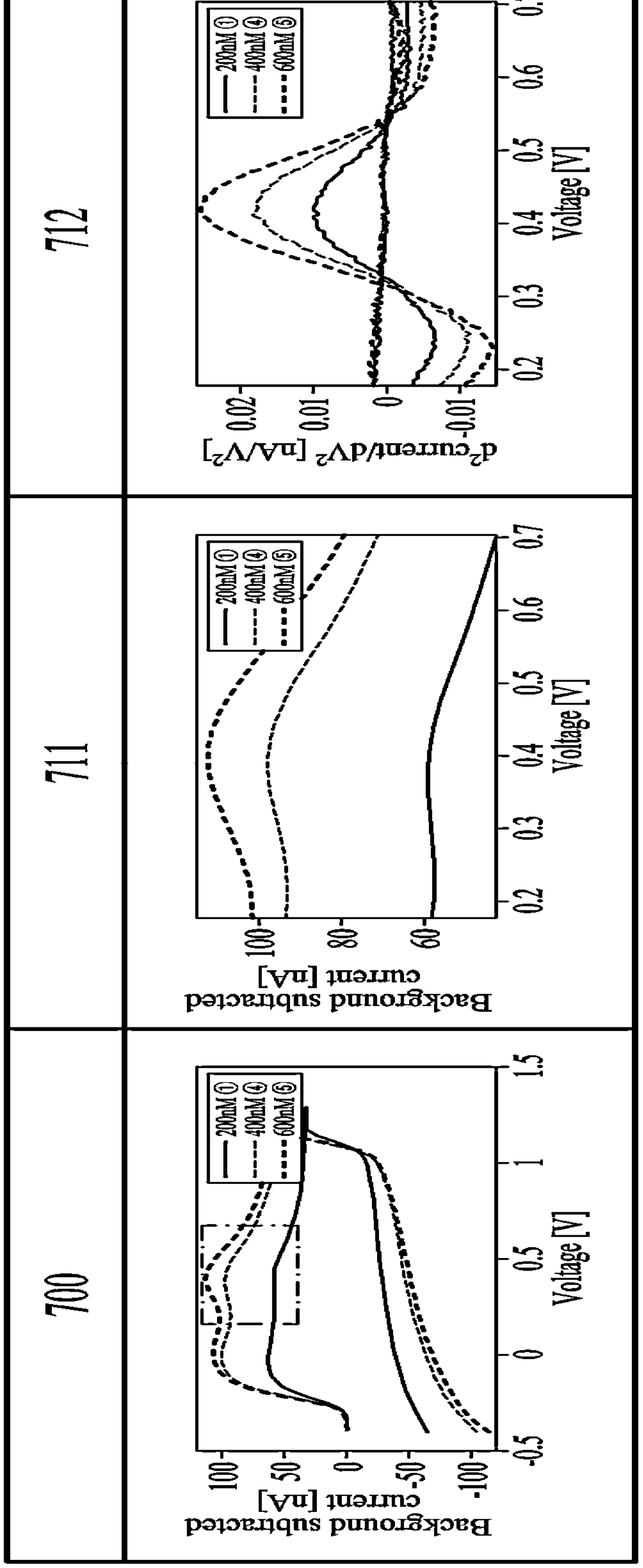

FIG. 7B shows voltammograms 10 minutes after dropping one drop of 200 nM dopamine (various concentrations of dopamine), specifically shows voltammogram changes with respect to ①, ④ and ⑤ shown in the graph 500 of FIG. 5.

Referring to FIG. 7B, a result obtained by applying the background subtraction technique to the dotted square part of a graph 710 corresponds to a graph 711, and the SDBR result of the graph 711 corresponds to a graph 712.

In the graph 711, it can be confirmed that the peak currents expressed in the three background-subtracted voltammograms are not linearly correlated with a dopamine concentration because it is contaminated by the capacitive current.

On the other hand, SDBRs in the graph 712 linearly show three different dopamine level changes according to the amplitude of the dopamine oxidation peak.

Figure 8A:
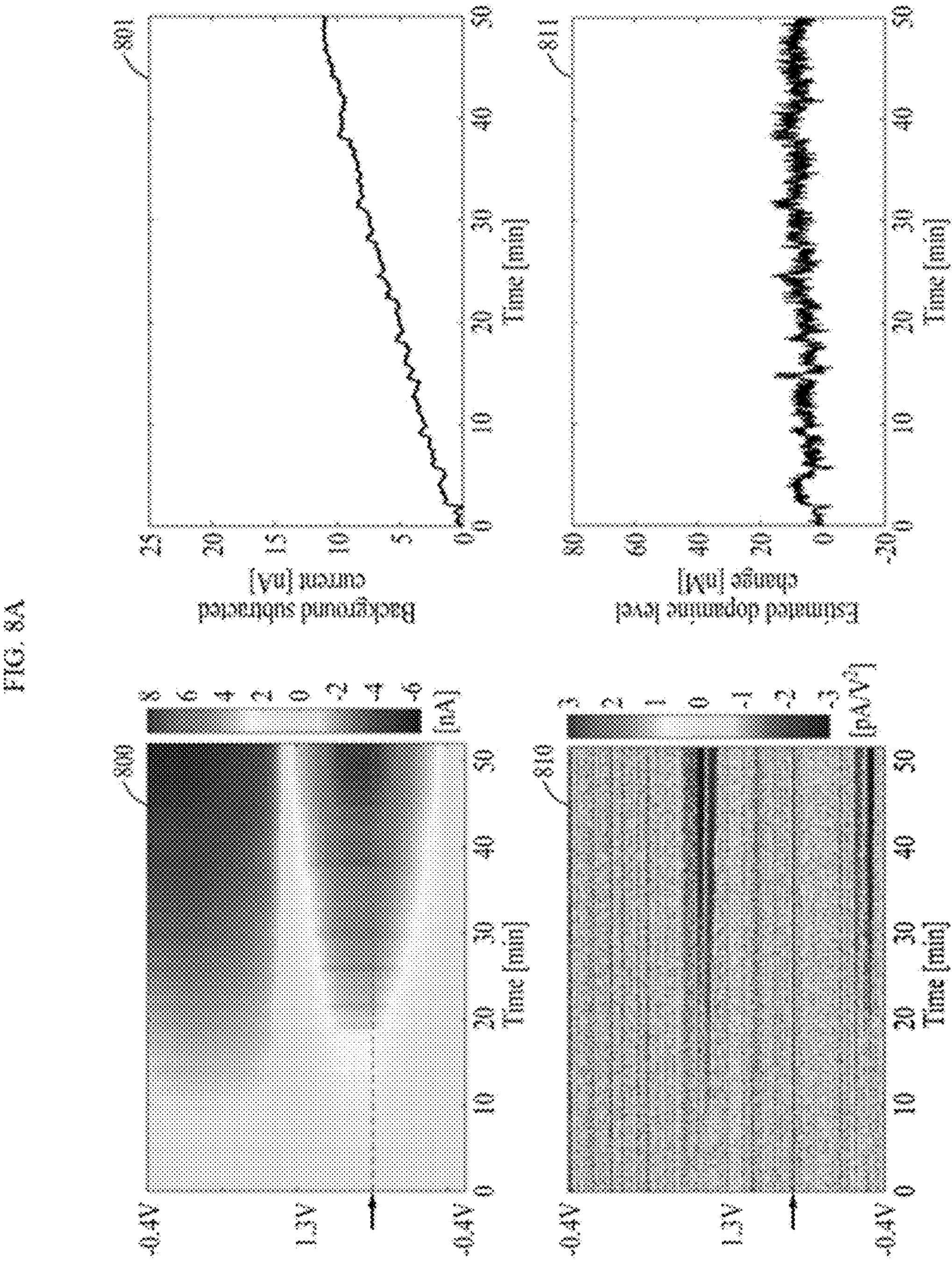
FIGS. 8A and 8B illustrate results of measuring a neurotransmitter concentration in an in vivo experiment using the neurotransmitter concentration measuring apparatus according to an embodiment of the present disclosure.
Figure 8B:
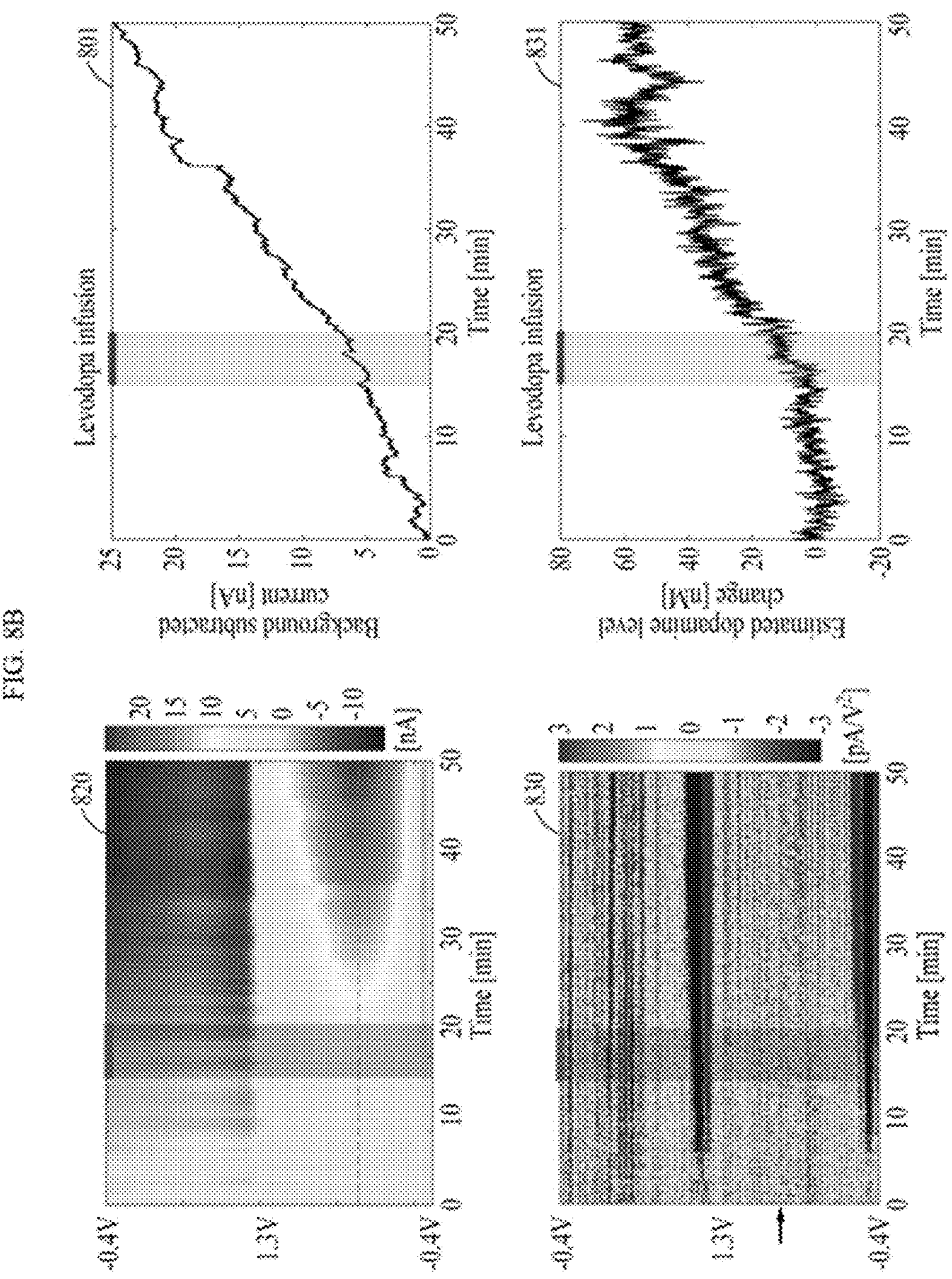

FIGS. 8A and 8B illustrate results of measuring a neurotransmitter concentration in an in vivo experiment using the neurotransmitter concentration measuring apparatus according to an embodiment of the present disclosure.

FIGS. 8A and 8B illustrate examples for confirming SDBR-based tonic dopamine measurement results, which can be confirmed through long-term measurement using standard FSCV data, through in vivo experiments by a neurotransmitter concentration measuring apparatus according to an embodiment of the present disclosure.

Referring to FIG. 8A, graphs 800 and 801 show background subtraction results, and graphs 802 and 803 show SDBR results.

The graphs 800 to 803 are shown to compare results measured in the striatum of healthy mice.

Referring to FIG. 8B, graphs 810 and 811 show background subtraction results, and graphs 812 and 813 show SDBR results.

The graphs 810 to 813 are shown to compare the results measured in the striatum of mice after levodopa infusion.

To confirm the practicality of SDBR in the in vivo environment, FSCV results after levodopa infusion of the striatum of healthy mice and the striatum of Parkinson's disease (PD) model (6-OHDA) mice are shown in FIGS. 8A and 8B.

From the graphs 800 and 801, it can be confirmed that the amplitude of the dopamine peak in the background subtraction result obtained by applying the background subtraction technique to the FSCV data measured in the striatum of healthy mice steadily increases.

However, the graphs 802 and 803 show that when SDBR is applied, the estimated dopamine concentration fluctuates within 10 nM over about 50 min.

Meanwhile, the graphs 810 to 813 of FIG. 8B show the results measured by FSCV in the striatum 15 minutes after levodopa was directly injected into the experimental mice, and the graphs 810 and 811 indicate that the amplitude of the dopamine peak consistently increases independent of drug infusion due to the background subtraction technique.

However, the graphs 812 and 813 showing SDBR results show a flat signal for about 15 minutes. Here, it can be confirmed that a dopamine concentration estimated immediately after levodopa infusion increases to 72.4 nM for about 25 minutes and then re-saturates.

Therefore, it can be confirmed through both types of in vivo experiments that SDBR can stably extract changes in a tonic dopamine concentration in vivo.

In Table 1, an existing technology and the data processing technology according to an embodiment of the present disclosure are compared and described.

TABLE 1

| Method | Time resolution | Detection limit (nM) | Simultaneous availability of phasic dopamine | Whether modification of waveform of standard FSCV is required |
|---|---|---|---|---|
| FSCAV | 20 s | 3.7 ± 0.5 | Partially | Y |
| CBM-FSCV | 10 s | 5.7 ± 0.9 | N | Y |
| Convolution-based current removal | 1 s | <40 | Y | Y |
| M-CSWV | 10 s | 0.17 ± 0.03 | N | Y |
| SWV | 15 s | 2.03 ± 0.09 | N | Y |
| SDBR | 0.1 s | 8.16 ± 0.08 | Y | N |

Since the SDBR implemented by the neurotransmitter concentration measuring apparatus according to an embodiment of the present disclosure is a post-processing technique applicable to standard FSCV, it has the advantage of being able to measure phase dopamine and tonic dopamine with high time resolution.

In addition, since the SDBR implemented by the neurotransmitter concentration measuring apparatus uses standard FSCV as it is, it may have versatility to extract tonic dopamine information from all FSCV data measured with standard FSCV.

The SDBR, implemented by the neurotransmitter concentration measuring apparatus, has sufficient detection limit performance to measure tonic dopamine changes associated with long-term changes.

In addition, the SDBR implemented by the neurotransmitter concentration measuring apparatus according to an embodiment of the present disclosure may improve both the analysis accuracy and detail of dopamine signals as it has improved time resolution compared to the existing technology.

Therefore, since the present disclosure extracts slow dopamine change information through post-processing while using the standard FSCV as it is, the present disclosure may additionally provide slow dopamine concentration change information to all standard FSCV data measured such that only fast dopamine concentration changes can be limitedly seen, by providing an additional slow dopamine change degree to fast dopamine information that can be measured with high sensitivity with the standard FSCV.

In addition, the present disclosure may improve the detailed analysis rate of a signal of dopamine, which is a neurotransmitter, because it can extract a faradaic current form of a neurotransmitter regardless of a capacitive charge current, thereby improving the temporal resolution.

Figure 9:
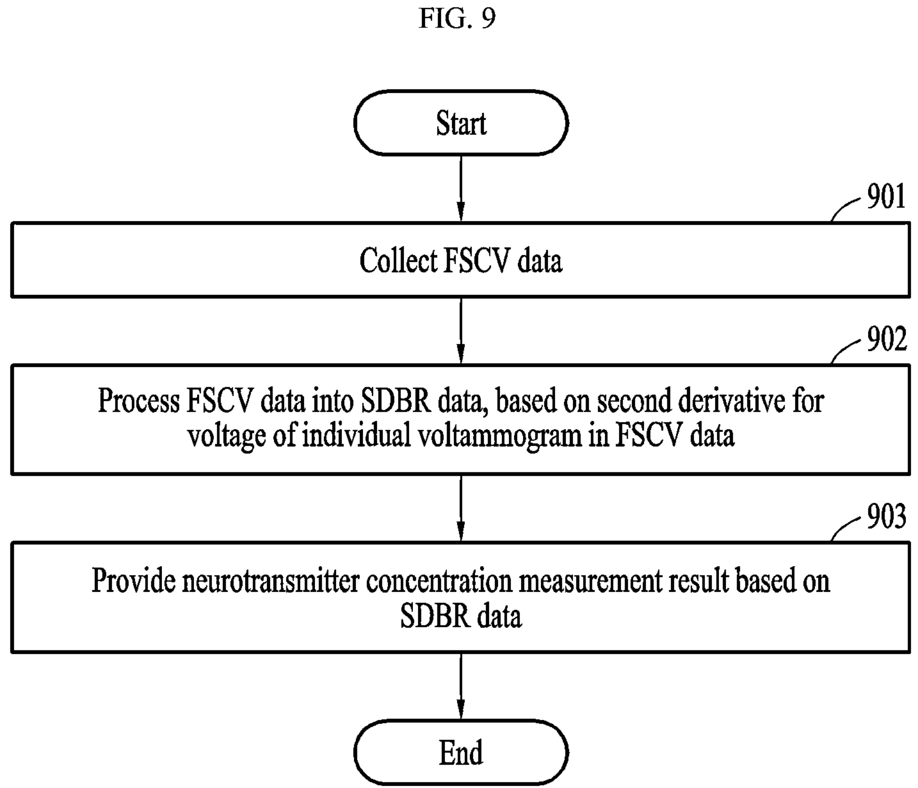
FIG. 9 illustrates a neurotransmitter concentration measurement method according to an embodiment of the present disclosure.

FIG. 9 illustrates a neurotransmitter concentration measurement method according to an embodiment of the present disclosure.

Referring to FIG. 9, the neurotransmitter concentration measurement method according to an embodiment of the present disclosure includes collecting FSCV data (step 901).

That is, the neurotransmitter concentration measurement method according to an embodiment of the present disclosure may collect the FSCV data in which a faradaic current increasing at the time of the neurotransmitter injection and the capacitive charge current gradually increasing over time are combined.

For example, since a faradaic current representing an increase in concentration according to the application of a neurotransmitter as the magnitude of a current and a capacitive charge current gradually increasing capacitively over time are combined in the FSCV data, data processing is required to confirm the concentration of the neurotransmitter.

In step 902 of the neurotransmitter concentration measurement method according to an embodiment of the present disclosure, the FSCV data may be processed into SDBR data based on the second derivative of the voltage of an individual voltammogram in the FSCV data.

That is, the neurotransmitter concentration measurement method according to an embodiment of the present disclosure may process FSCV data into faradaic current-type SDBR data, from which the capacitive charge current is subtracted, based on the second derivative of the voltage of an individual voltammogram generated for each scan by background subtraction from the FSCV data.

More specifically, the neurotransmitter concentration measurement method may extract the individual voltammogram in which the faradaic current and the capacitive charge current are reflected together for each scan by the background subtraction in relation to a peak according to neurotransmitter injection in the FSCV data, and process as the SDBR data by quantifying a curvature of a neurotransmitter peak by multiplying the extracted individual voltammogram by a negative value after the second derivative for the voltage of the extracted individual voltammogram.

In step 903 of the neurotransmitter concentration measurement method according to an embodiment of the present disclosure, the neurotransmitter concentration measurement result may be provided based on the SDBR data.

That is, the neurotransmitter concentration measurement method according to an embodiment of the present disclosure may determine a faradaic current shape-based neurotransmitter oxidation peak voltage, from which the capacitive charge current has been subtracted, based on SDBR data, and may provide a neurotransmitter concentration, compared to the determined neurotransmitter oxidation peak voltage, as a neurotransmitter concentration measurement result.

Therefore, the present disclosure can improve the accessibility of neuroscientists who want to measure the concentration of a neurotransmitter using the standard FSCV data because the input voltage waveform of the standard FSCV can be used as it is.

As apparent from the above description, the present invention can provide a technology of extracting faradaic current-type Second-Derivative-based Background Removal (SDBR) data, from which a capacitive charge current is subtracted, through second derivative after background subtraction of FSCV data and providing a neurotransmitter concentration measurement result based on the extracted SDBR data.

In addition, since the present disclosure extracts slow dopamine change information through post-processing while using the standard FSCV as it is, the present disclosure can additionally provide slow dopamine concentration change information to all standard FSCV data measured such that only fast dopamine concentration changes can be limitedly seen, by providing an additional slow dopamine change degree to fast dopamine information that can be measured with high sensitivity with the standard FSCV.

In addition, the present disclosure can improve the accessibility of neuroscientists who want to measure the concentration of a neurotransmitter using the standard FSCV data because the input voltage waveform of the standard FSCV can be used as it is.

Further, the present disclosure can improve the detailed analysis rate of a signal of dopamine, which is a neurotransmitter, because it can extract a faradaic current form of a neurotransmitter regardless of a capacitive charge current, thereby improving the temporal resolution.

The apparatus described above may be implemented as a hardware component, a software component, and/or a combination of hardware components and software components. For example, the apparatus and components described in the embodiments may be achieved using one or more general purpose or special purpose computers, such as, for example, a processor, a controller, an arithmetic logic unit (ALU), a digital signal processor, a microcomputer, a field programmable array (FPA), a programmable logic unit (PLU), a microprocessor, or any other device capable of executing and responding to instructions. The processing device may execute an operating system (OS) and one or more software applications executing on the operating system. In addition, the processing device may access, store, manipulate, process, and generate data in response to execution of the software. For ease of understanding, the processing apparatus may be described as being used singly, but those skilled in the art will recognize that the processing apparatus may include a plurality of processing elements and/or a plurality of types of processing elements. For example, the processing apparatus may include a plurality of processors or one processor and one controller. Other processing configurations, such as a parallel processor, are also possible.

The methods according to the embodiments of the present invention may be implemented in the form of a program command that can be executed through various computer means and recorded in a computer-readable medium. The computer-readable medium can store program commands, data files, data structures or combinations thereof. The program commands recorded in the medium may be specially designed and configured for the present invention or be known to those skilled in the field of computer software. Examples of a computer-readable recording medium include magnetic media such as hard disks, floppy disks and magnetic tapes, optical media such as CD-ROMs and DVDs, magneto-optical media such as floptical disks, or hardware devices such as ROMs, RAMs and flash memories, which are specially configured to store and execute program commands. Examples of the program commands include machine language code created by a compiler and high-level language code executable by a computer using an interpreter and the like. The hardware devices described above may be configured to operate as one or more software modules to perform the operations of the embodiments, and vice versa.

The software may include computer programs, code, instructions, or a combination of one or more of the foregoing, configure the processing apparatus to operate as desired, or command the processing apparatus, either independently or collectively. In order to be interpreted by a processing device or to provide instructions or data to a processing device, the software and/or data may be embodied permanently or temporarily in any type of a machine, a component, a physical device, a virtual device, a computer storage medium or device, or a transmission signal wave. The software may be distributed over a networked computer system and stored or executed in a distributed manner. The software and data may be stored in one or more computer-readable recording media.

Although the present invention has been described with reference to limited embodiments and drawings, it should be understood by those skilled in the art that various changes and modifications may be made therein. For example, the described techniques may be performed in a different order than the described methods, and/or components of the described systems, structures, devices, circuits, etc., may be combined in a manner that is different from the described method, or appropriate results may be achieved even if replaced by other components or equivalents.

Therefore, other embodiments, other examples, and equivalents to the claims are within the scope of the following claims.

What is claimed is:

1. A neurotransmitter concentration measuring apparatus comprising:

a data collector configured to collect Fast-Scan Cyclic Voltammetry (FSCV) data in which a capacitive charge current is reflected in a faradaic current that changes according to neurotransmitter injection;

a data processor configured to:

extract the individual voltammogram in which the faradaic current and the capacitive charge current are reflected together for each scan by the background subtraction in relation to a peak voltage generated based on neurotransmitter injection in the FSCV data; and process the FSCV to convert the FSCV data to a faradaic current-type Second-Derivative-based Background Removal (SDBR) data, in which the capacitive charge current is subtracted from the FSCV data, based on a second derivative for a voltage of the individual voltammogram, wherein the processing of the FSCV data comprises quantifying a curvature of a neurotransmitter peak by multiplying the extracted individual voltammogram by a negative value after the second derivative for the voltage of the extracted individual voltammogram; and a measurement result provider configured to provide a concentration measurement result of a neurotransmitter that changes according to the neurotransmitter injection based on the SDBR data.

2. The neurotransmitter concentration measuring apparatus according to claim 1, wherein the extracted individual voltammogram comprises a phasic measurement result in relation to measuring a concentration of the neurotransmitter, and the SDBR data comprises the phasic measurement result and tonic measurement result in relation to measuring a concentration of the neurotransmitter.

3. The neurotransmitter concentration measuring apparatus according to claim 1, wherein the data processor extracts the individual voltammogram such that, after the background subtraction, a voltammogram around a neurotransmitter oxidation peak has a symmetrical Gaussian shape.

4. The neurotransmitter concentration measuring apparatus according to claim 3, wherein the data processor processes the SDBR data such that an amplitude current of a neurotransmitter oxidation peak of a voltammogram corresponding to the individual voltammogram is linearly correlated with a concentration of the neurotransmitter and such that a background charging current generated around the neurotransmitter oxidation peak is independent of voltage.

5. The neurotransmitter concentration measuring apparatus according to claim 1, wherein the measurement result provider determines a neurotransmitter oxidation peak voltage based on the faradaic current from which the capacitive charge current based on the SDBR data is subtracted, and provides a neurotransmitter concentration measurement result based on the determined neurotransmitter oxidation peak voltage.

6. The neurotransmitter concentration measuring apparatus according to claim 1, wherein the data collector collects the FSCV data in which a faradaic current increasing at a time of the neurotransmitter injection and the capacitive charge current gradually increasing over time are combined.

7. A neurotransmitter concentration measurement method comprising:

collecting, by a data collector, Fast-Scan Cyclic Voltammetry (FSCV) data in which a capacitive charge current is reflected in a faradaic current that changes according to neurotransmitter injection;

extracting, by a data processor, the individual voltammogram in which the faradaic current and the capacitive charge current are reflected together for each scan by the background subtraction in relation to the peak voltage generated based on neurotransmitter injection in the FSCV data;

processing, by the data processor, the FSCV data to convert the FSCV data to a faradaic current-type Second-Derivative-based Background Removal (SDBR) data, in which the capacitive charge current is subtracted from the FSCV data based on a second derivative for a voltage of the individual voltammogram, wherein the processing of the FSCV data comprises quantifying a curvature of a neurotransmitter peak by multiplying the extracted individual voltammogram by a negative value after the second derivative for the voltage of the extracted individual voltammogram; and providing, by a measurement result provider, a concentration measurement result of a neurotransmitter that changes according to the neurotransmitter injection based on the SDBR data.

8. The neurotransmitter concentration measurement method according to claim 7, wherein the extracted individual voltammogram comprises a phasic measurement result in relation to measuring a concentration of the neurotransmitter, and the SDBR data comprises the phasic measurement result and tonic measurement result in relation to measuring a concentration of the neurotransmitter.

9. The neurotransmitter concentration measurement method according to claim 7, wherein the converting comprises:

extracting the individual voltammogram such that, after the background subtraction, a voltammogram around a neurotransmitter oxidation peak has a symmetrical Gaussian shape; and processing the SDBR data such that an amplitude current of a neurotransmitter oxidation peak of a voltammogram corresponding to the individual voltammogram is linearly correlated with a concentration of the neurotransmitter and such that a background charging current generated around the neurotransmitter oxidation peak is independent of voltage.

10. The neurotransmitter concentration measurement method according to claim 7, wherein the providing comprises determining a neurotransmitter oxidation peak voltage based on the faradaic current from which the capacitive charge current based on the SDBR data is subtracted; and providing a neurotransmitter concentration measurement result based on the determined neurotransmitter oxidation peak voltage.

11. The neurotransmitter concentration measurement method according to claim 7, wherein the collecting comprises collecting the FSCV data in which a faradaic current increasing at a time of the neurotransmitter injection and the capacitive charge current gradually increasing over time are combined.

* * * * *